United States Patent [19]

Kim

[11] Patent Number: 4,814,463

[45] Date of Patent: Mar. 21, 1989

[54] CCK ANTAGONISTS

[75] Inventor: Sun H. Kim, Chestnut Hill, Mass.

[73] Assignee: Biomeasure, Inc., Hopkinton, Mass.

[21] Appl. No.: 815,217

[22] Filed: Dec. 31, 1985

[51] Int. Cl.$^4$ .............................................. C07K 5/06
[52] U.S. Cl. ................................... 548/495; 260/998.2; 514/19
[58] Field of Search ................... 548/495; 260/998.2; 514/19

[56] References Cited

U.S. PATENT DOCUMENTS 4,000,297 12/1976 Rovati et al. ..................... 424/274
4,356,118 10/1982 Owens ............................. 260/998.2
4,518,587 5/1985 Laruelle et al. ................. 260/998.2

OTHER PUBLICATIONS

Chang et al., 11, (1985) Science 230:177-179.

Primary Examiner—David B. Springer

[57] ABSTRACT

In general, the invention features CCK antagonist compounds having the formula:

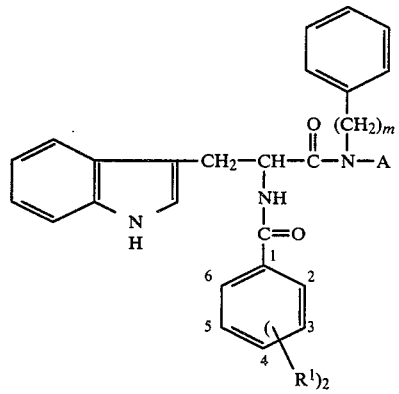

or a pharmaceutically acceptable salt thereof, wherein each $R^1$ is, independently, an alkyl group having 1 to 5, inclusive, carbon atoms, an alkoxy group having 1 to 5, inclusive, carbon atoms, a halogen, amino, hydroxy, nitro, cyano, carboxyl, trifluoromethyl, ethyl carboxylate, or a hydrogen; m is an integer between 0 and 2, inclusive; and A is either

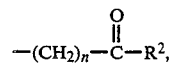

where n is an integer between 1 and 5, inclusive, and $R^2$ is hydroxy, an alkoxy group having 1 to 5, inclusive, carbon atoms, aralkoxy (e.g., benzyloxy), aralkyl (e.g., benzyl), amino, an alkyl group having 1 to 5, inclusive, carbon atoms, an alkylamino group having 1 to 5, inclusive, carbon atoms, a dialkylamino group with each alkyl group, independently having 1 to 5, inclusive, carbon atoms, a cycloalkylamino group wherein the ring has 4 to 6, inclusive, carbon atoms (e.g., pyrrolidino, piperidino, N-methylpiperazino), or morpholino; or A is an alkyl group having 1 to 5, inclusive, carbon atoms, a hydroxyalkyl group having 1 to 5, inclusive, carbon atoms, an alkoxyalkyl group having 2 to 8, inclusive, carbon atoms, an aralkoxyalkyl having 8 to 14, inclusive, carbon atoms, in aryl group (e.g., phenyl, toluyl) having 6 to 14, inclusive, carbon atoms, an aralkyl group (e.g., benzyl, phenylethyl) having 6 to 14, inclusive, carbon atoms, and a cycloalkyl group having 3 to 12, inclusive, carbon atoms.

17 Claims, No Drawings

CCK ANTAGONISTS

BACKGROUND OF THE INVENTION

This invention relates to cholecystokinin (CCK) antagonists.

Chang et al., 230 *Science* 177 (1985), describes CCK as "a hormonal regulator of pancreatic and gastric secretion, contraction of the gallbladder, and gut motility," and states that "CCK also exists in the brain and may have an equally important role as a central nervous system transmitter." Chang et al. further mentions that CCK antagonists have "potential therapeutic utilities" and describes the compound asperlicin, which has the structure

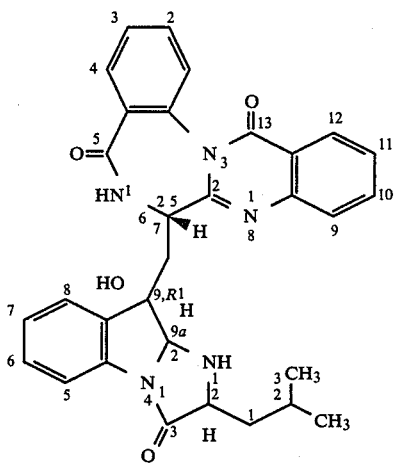

as a CCK antagonist.

Rovati et al., U.S. Pat. No. 4,000,297, discloses compounds of the structure

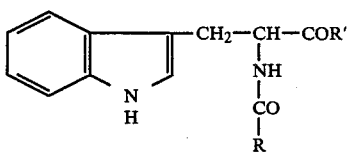

in which R includes mono and poly substituted phenyl goups, and R' includes hydroxyl, an aniline group substituted at the para position with a carboxylic acid or ester thereof, an amino group substituted with phenylacetic acid or ester derivative thereof, or a alkoxy group terminting with an amino group. The compounds are described as having an antispastic effect on the smooth muscle of the gastroenteric tract, as regulating gastric secretion, and as being protective of gastroenteric mucosa.

SUMMARY OF THE INVENTION

In general, the invention features compounds having the formula:

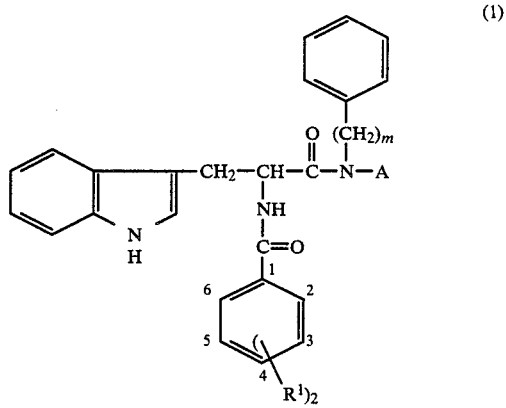

(1)

or a pharmaceutically acceptable salt thereof, wherein each $R^1$ is, independently, an alkyl group having 1 to 5, inclusive, carbon atoms, an alkoxy group having 1 to 5, inclusive, carbon atoms, a halogen, amino, hydroxy, nitro, cyano, carboxyl, trifluoromethyl, ethyl carboxylate, or a hydrogen; m is an integer between 0 and 2, inclusive; and A is either

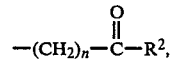

where n is an integer between 1 and 5, inclusive, and $R^2$ is hydroxy, an alkoxy group having 1 to 5, inclusive, carbon atoms, aralkoxy (e.g., benzyloxy), aralkyl (e.g., benzyl), amino, an alkyl group having 1 to 5, inclusive, carbon atoms, an alkylamino group having 1 to 5, inclusive, carbon atoms, a dialkylamino group with each alkyl group, independently, having 1 to 5, inclusive, carbon atoms, a cycloalkylamino group wherein the ring has 4 to 6, inclusive, carbon atoms (e.g., pyrrolidino, piperidino, N-methylpiperazino), or morpholino; or A is an alkyl group having 1 to 5, inclusive, carbon atoms, a hydroxyalkyl group having 1 to 5, inclusive, carbon atoms, an alkoxyalkyl group having 2 to 8, inclusive, carbon atoms, an aralkoxyalkyl having 8 to 14, inclusive, carbon atoms, an aryl group (e.g., phenyl, toluyl having 6 to 14, inclusive, carbon atoms, an aralkyl group (e.g., benzyl, phenylethyl) having 6 to 14, inclusive, carbon atoms, and a cycloalkyl group having 3 to 12, inclusive, carbon atoms.

In preferred embodiments of the invention, the tryptophan residue is of the L-configuration, the $R^1$'s are either both hydrogen, both chloro (at the 3 and 4 position of the ring), or one hydrogen and one chloro (at the 4 position). Preferred compounds of the invention include N-benzoyl-L-tryptyl-N'-benzylglycine, N-benzoyl-L-tryptyl-N'-benzylglycine ethylester, N-benzoyl-L-tryptyl-N'-benzylglycineamide, N-(4-chlorobenzoyl)-L-tryptyl-N'-benzylglycine, N-(4-chlorobenzoyl)-L-tryptyl-N'-benzylglycine ethylester, N-(4-chlorobenzoyl)-L-tryptyl-N'-benzylglycineamide, N-(3,4-dichlorobenzoyl)-L-tryptyl-N'-benzylglycineamide, N-(3,4-dichlorobenzoyl)-L-tryptyl-N'-benzylglycine ethylester, N-(3,4-dichlorobenzoyl)-L-tryptyl-N'-benzylglycineamide, N-benzoyl-L-tryptyl-N'-benzyl-N'-methylamide, N-(4-chlorobenzoyl)-L-tryptyl-N'-benzyl-N'-methylamide, N-(3,4-dichlorobenzoyl)-N'-benzyl-N'-methylamide; or pharmaceutically acceptable salts thereof.

In other preferred embodiments, a therapeutically effective amount of therapeutic compound and a pharmaceutically acceptable carrier substance, e.g., magnesium carbonate or lactose, form a therapeutic composition, e.g., a pill, tablet, capsule, or liquid, for oral administration to a patient; a liquid or an ointment capable of being administered transdermally, nasally, rectally, or sublingualy; a liquid capable of being administered intravenously, parenterally, subcutaneously, or intraperitonally; or an oral or a parenteral sustained release formulation.

The compounds of the invention are effective cholecystokinin antagonists and as such are effective in treating acute pancreatitis; in treating gastric, peptic, and duodenal ulcers; and in suppressing appetite. They are stable, inexpensive to make, and non-toxic.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

STRUCTURE

The compounds of the invention have the general formula recited in the summary of the invention above. Examples of preferred compounds within this formula are those referred to as preferred embodiments above.

The compounds of the invention are N-substituted (D- or L-) tryptyl N'-disubstituted glycine or N-substituted (D- or L-) tryptyl N'-disubstituted amide derivatives.

The compounds can also be provided in the form of pharmaceutically acceptable salts. Examples of suitable salts include those formed with hydrochloric, hydrobromic, sulfuric, maleic, acetic, or fumaric acid; potassium, sodium, or aluminum hydroxide; or dicyclohexylamine.

SYNTHESIS

The above compounds can be synthesized as follows. First, a compound of formula (2)

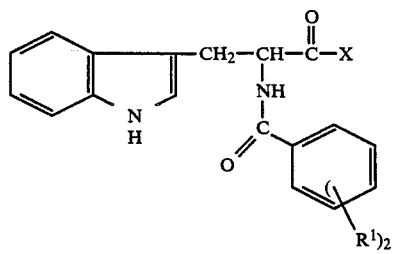

where X represents a hydroxyl or carboxylic acid activating group, e.g., a halogen such as chlorine, and $R^1$ is defined as above, is condensed with a secondary amino compound of formula (3)

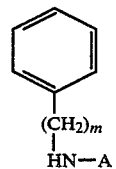

where m and A are defined as before.

The corresponding acids are then prepared from these esters by hydrolyzing the esters with aqueous base. Amides can be prepared by treating the corresponding esters with ammonia or an amine.

Compounds within formulae (2) and (3) are commercially available; alternatively they can be synthesized according to standard methods, e.g., as described in Greenstein, et al., *Chemistry of the Amino Acids*, Vols. 1–3, J. Wiley, New York (1961); *J. Pharm. Sce.*, 51, 1058 (1962); *Org. Reaction* 5, 301 (1949); *J. Chem. Soc.* (c), 2223 (1969); and *J. Org. Chem.*, 37, 1673 (1972).

The condensation reactions are preferably carried out in an inert organic solvent, e.g., dimethylformamide, dichloromethane, tetrahydrofuran, benzene, or acetonitrile, using a suitable mild condensing agent, e.g., thionylchoride, oxalylchloride, or dicyclohexylcarbodiimide (DCC), and optionally a catalyst, e.g., 1-hydroxybenzotriazole (HOBT). The reaction temperature is maintained below room temperature ($-15°$ C. to room temperature) in order to minimize side reactions. Typical condensation procedures are described in Schroeder et al., *The Peptides*, Vols. 1–2 (1965, 1966) and Gross et al., *The Peptides*, Vols. 1–3 (1979, 1980, 1981).

The intermediate and final products are isolated and purified by standard methods e.g., column chromatography or crystallization. Purity is determined using chromatographic, spectroscopic, and chemical analysis.

Specific compounds are made as follows.

N-Benzoyl-L-tryptyl-N'-benzylglycine ethylester

The first step is the preparation of N-benzoyl-L-tryptophan, as follows. 10 ml benzoyl chloride and 45 ml 2N NaOH are added, in several and alternate portions, to a vigorously stirred and ice-cooled solution of 17 g L-tryptophan in 41 ml 2N NaOH. The solution is maintained at an alkaline pH by the addition of extra base when necessary. Upon completion of the addition of reagents, the mixture is stirred at room temperature for 1 hour, after which it is acidified to pH 1–2 with HCl. The crude product is dried and then triturated with cold ether to give ;b 20 g of the product as a colorless solid. TLC: (silica gel; $CHCL_3/MeOH/HoAC=6:1:0.25$) $Rf=0.53$.

A cold solution of 1.44 g dicyclohexylcarbodiimide in 4 ml dimethylformamide is added to a stirred ice-cooled solution of 2.0 g N-benzoyl-L-tryptophan and 1.26 g N-benzylglycine ethylester in 8 ml dry dimethlformamide. The resulting mixture is stirred at 0° C. for 1 hour and then at room temperature overnight. It is then filtered and the solvent is evaporated to dryness in vacuo. The residue is partitioned between chloroform and water. The chloroform layer is washed with 5% aqueous $NaHCO_3$ and water, and then dried over anhydrous $MgSO_4$. After evaporation of solvent, the residue is chromatographed on silica gel (250 g) using chloroform/acetone (19:1). Appropriate fractions are pooled and the solvent removed in vacuo to yield 1.55 g of the product as a foam. TLC: (silica gel; CHCl3/acetone<9:1) Rf=0.35.

N-Benzoyl-L-tryptyl-N'-benzylglycineamide

The first step is the preparation of N-(4-chlorobenzoyl)-L-tryptophan in an analogous manner to the preparation of N-benzoyl-L-tryptophan except substituting 4-chlorobenzoyl chloride (dissolved in either dioxane, tetrahydrofuran, or acetone) for benzoyl chloride.

490 mg N-benzoyl-L-tryptyl-N'-benzylglycine ethylester is dissolved in 10 ml saturated methanolic ammonia, and the solution is kept at room temperature in a pressure bottle overnight. Excess ammonia and solvent are then removed in vacuo, and the residue is recrytalized from ethanol to yield 286 mg of the crystalline product. m.p. 203°-204°; TLC: (silica gel; CHCl3/MeOH=9:1) Rf =0.47.

N-Benzoyl-L-tryptyl-N'-benzylglycine 500 mg N-benzoyl-L-tryptyl-N'-benzylglycine ethylester is dissolved in 5 ml ethanol and treated with 1 ml 2N NaOH. After stirring at room temperature for 1 hour, the solution is diluted with water, acidified to pH 1-2 with 2N HCl, and extracted with ethylacetate (3×50 ml). The combined extracts are dried over anhydrous MgSO4, and solvent is removed in vacuo to yield 440 mg of the product as a foam. TLC: (silica gel; CHCl3/MeOH/HoAC=6:1:0.25) Rf=0.6.

N-(3,4-Dichlorobenzoyl)-L-tryptyl-N'-benzylglycine ethylester

The first step is the preparation of N-(3,4-dichlorobenzoyl)-L-tryptophan in an analogous manner to the preparation of N-beenzoyl-L-tryptophan except substituting 3,4-dichlorobenzoyl chloride (dissolved in either dioxane, tetrahydrofuran, or acetone) for benzoyl chloride.

A cold solution of 1.74 g dicyclohexylcarbodiimide in 2 ml dimethlformamide is added to a stirred ice-cooled solution of 3.0 g N-(3,4-dichlorobenzoyl)-L-tryptophan, 1.55 g N-benzylglycine ethylester, and 2.1 g 1-hydroxybenzotriazole in 10 ml dimethylformamide. The mixture is stirred at 0° C. for 1 hour and then at room temperature for 2 hours. It is then filtered, and the solvent is evaporated in vacuo to dryness. The residue is dissolved in chloroform, washed with 5% aqueous NaHCO3 and water, and dried over anhydrous MgSO4. Solvent is evaporated in vacuo to dryness and the residue is dissolved in chloroform, washed with 5% aqueous NaHCO3 and water, and dried over anhydrous MgSO4. After evaporation of solvent, the residue is chromatographed on silica gel (260 g) using CHCl3/acetone (40:1) as the eluent. Appropriate fractions are pooled and the solvent removed in vacuo to yield 2.4 g of the product as a colorless solid. m.p. 190°-192°; tlc: (silica gel; CHCl3/acetone=9:1) Rf=0.42.

N-Benzoyl-L-tryptyl-N'-benzyl-N'-methylamide

A cold solution of 0.5 g dicyclohexylcarbodiimide in 2 ml dichloromethane is added to a stirred ice-cooled solution of 0.6 g N-benzoyl-L-tryptophan and 0.3 g N-benzylmethylamine in dichloromethane dimethylformide (2:1, 20 ml). The mixture is stirred at 0° C. for 1 hour and then at room temperature overnight. It is then filtered and the solvent evaporated in vacuo to dryness. The residue is partitioned between chloroform and water. The chloroform layer is washed with 5% NaHCO3 and water, and then dried over anhydrous MgSO4. After evaporation of solvent, the residue is chromatographed on silica gel (35 g) using chloroform/acetone (19:1). Appropriate fractions are pooled and the solvent removed in vacuo to yield 0.57 g of the product as colorless solid. m.p. 65°-68°; TLC (Silica gel; CHCl3/acetone=4:0) Rf=0.45.

USE

When administered to a patient (e.g., orally, intravenously, parenterally, nasally, or by suppository), the compounds are effective in the treatment of gastric, peptic, and duodenal ulcers; in the treatment of acute pancreatitis; and in suppressing appetite.

The compounds can be administered to a human patient in a dosage of 0.1-50 mg/kg/day, preferably about 0.1 mg/kg/day when administered parenterally and about 50 mg/kg/day when administered orally.

Other embodiments are within the following claims.

I claim:

1. A compound having the formula

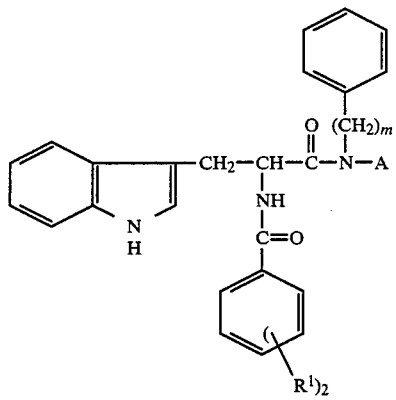

or a pharmaceutically acceptable salt thereof, wherein each $R^1$ is, indpendently, an alkyl group having 1-5, inclusive, carbon atoms, an alkoxy group having 1-5, inclusive, carbon atoms, a halogen amino, hydroxy, nitro, cyano, carboxyl, trifluoromethyl, ethyl carboxylate, or a hydrogen;

m is an integer between 0 and 2, inclusive;

A is either

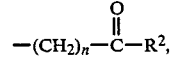

wherein n is an integer between 1 and 5, inclusive, and $R^2$ is hydroxy, an alkoxy group having 1 to 5, inclusive, carbon atoms, aralkoxy and aralkyl, each having 6-14 inclusive, carbon atoms, amino, an alkyl group having 1 to 5, inclusive, carbon atoms, an alkylamino group having 1 to 5, inclusive, carbon atoms, a dialkylamino group with each alkyl group having 1 to 5, inclusive, carbon atoms, or pyrrolidino; or A is an alkyl group having 1 to 5, inclusive, carbon atoms, a hydroxyalkyl group having 1 to 5, inclusive, carbon atoms, an alkoxyalkyl group having 2 to 8, inclusive, carbon atoms, an aralkoxyalkyl having 8 to 14, inclusive, carbon atoms, an aryl group having 6 to 14, inclusive, carbon atoms, an aralkyl group having 6 to 14, inclusive, carbon atoms, and a cycloalkyl group having 3-12, inclusive, carbon atoms.

2. The compound of claim 1 wherein the tryptophan residue is of the L-configuration, both $R^1$'s are H, m is 1, and A is

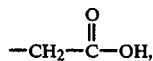

said compound having the name N-benzyol-L-tryptyl-N'-benzylglycine; or a pharmaceutically acceptable salt thereof.

3. The compound of claim 1 wherein the tryptophan residue is of the L-configuration, both $R^1$'s are H, m is 1, and A is

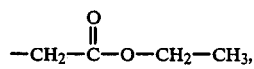

said compound having the name N-benzoyl-L-tryptyl-N'-benzylglycine ethylester; or a pharmaceutically acceptable salt thereof.

4. The compound of claim 1 wherein the tryptophan residue is of the L-configuration, both $R^1$'s are H, m is 1, and A is

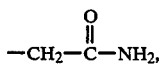

said compound havinf the name N-benzoyl-L-tryptyl-N'-benzylglycineamide; or a pharmaceutically acceptable salt thereof.

5. The compound of claim 1 wherein the tryptophan residue is of the L-configuration, one $R^1$ is H, the other $R^1$ is 4-chloro, m is 1, and A is

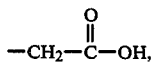

said compound having the name N-(4-chlorobenzoyl)-L-tryptyl-N'-benzylglycine; or a pharmaceutically acceptable salt thereof.

6. The compound of claim 1, wherein the tryptophan residue is of the L-configuration, one $R^1$ is H, the other $R^1$ is 4-chloro, m is 1, and A is

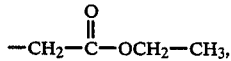

said compound having the name N-(4-chlorobenzoyl)-L-tryptyl-N'-benzylglycine ethylester; or a pharmaceutically acceptable salt thereof.

7. The compound of claim 1, wherein the tryptophan residue is of the L-configuration, one $R^1$ is H, the other $R^1$ is 4-chloro, m is 1, and A is

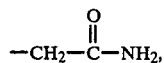

said compound having the name N-(4-chlorobenzoyl)-L-tryptyl-N'-benzylglycineamide; or a pharmaceutically acceptable salt thereof.

8. The compound of claim 1, wherein the tryptophan residue is of the L-configuration, one $R^1$ is 3-chloro, the other $R^2$ is 4-chloro, m is 1, and A is

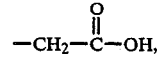

said compound having the name N-(3,4-dichlorobenzoyl)-L-tryptyl-N'-benzylglycine; or a pharmaceutically acceptable salt thereof.

9. The compound of claim 1 wherein the tryptophan residue is of the L-configuration, one $R^1$ is 3-chloro, the other $R^1$ is 4-chloro, m is 1, and A is

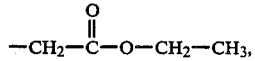

said compound having the name N-(3,4-dichlorobenzoyl)-L-tryptyl-N'-benzylglycine ethylester; or a pharmaceutically acceptable salt thereof.

10. The compound of claim 1 wherein the tryptophan residue is of the L-configuration, one $R^1$ is 3-chloro, the other $R^1$ is 4-chloro, m is 1, and A is

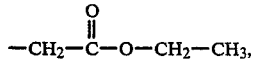

said compound having the name N-(3,4-dichlorobenzoyl)-L-tryptyl-N'-benzylglycineamide; or a pharmaceutically acceptable salt thereof.

11. The compound of claim 1 wherein the tryptophan reside is of the L-configuration, both $R^1$'s are H, m is 1, and A is —$CH_3$, said compound having the name N-benzoyl-L-tryptyl-N'-benzyl-N'-methylamide; or a pharmaceutically acceptable salt thereof.

12. The compound of claim 1 wherein the tryptohan residue is of the L-configuration, one $R^1$ is H, the other $R^1$ is 4-chloro, m is 1, and A is —$CH_3$, said compound having the name N-(4-chlorobenzoyl)-L-tryptyl-N'-benzyl-N'-methylamide; or a pharmaceutically acceptable salt thereof.

13. The compound of claim 1 wherein the tryptophan residue is of the L-configuration, one $R^1$ is 3-chloro, the other $R^1$ is 4-chloro, m is 1, and A is —$CH_3$, said compound having the name N-(3,4-dichlorobenzoyl)-L-tryptyl-N'-benzyl-N'-methylamide; or a pharmaceutically acceptable salt thereof.

14. The compound of claim 1, wherein said aralkoxy is benzyloxy.

15. The compound of claim 1, wherein said $R^2$ is benzyl.

16. The compound of claim 1 wherein said aryl group is phenyl or toluyl.

17. The compound of claim 1 wherein said A is benzyl or phenylethyl.

* * * * *

UNITED STATES PATENT AND TRADEMARK OFFICE
CERTIFICATE OF CORRECTION

PATENT NO. : 4,814,463
DATED : March 21, 1989
INVENTOR(S) : Sun H. Kim

It is certified that error appears in the above-identified patent and that said Letters Patent is hereby corrected as shown below:

Column 8, line 35, change the chemical structure

" $CH_2-\overset{\overset{O}{\|}}{C}-O-CH_2-CH_3$ "

to read

-- $CH_2-\overset{\overset{O}{\|}}{C}-NH_2$ --

Signed and Sealed this

Fifth Day of June, 1990

Attest:

HARRY F. MANBECK, JR.

*Attesting Officer*      *Commissioner of Patents and Trademarks*